United States Patent [19]
Boarman

[11] Patent Number: 5,113,873
[45] Date of Patent: * May 19, 1992

[54] CONTRACEPTION AND PROPHYLAXIS ENHANCEMENT SYSTEM

[76] Inventor: George L. Boarman, 13187 Highland Rd., Highland, Md. 20777

[ * ] Notice: The portion of the term of this patent subsequent to May 30, 2006 has been disclaimed.

[21] Appl. No.: 532,568

[22] Filed: Jun. 4, 1990

[51] Int. Cl.$^5$ .............................. A61F 6/06; A61F 6/04
[52] U.S. Cl. ................................. 128/830; 128/844; 128/918
[58] Field of Search ................. 128/842, 844, 79, 830, 128/918; 604/330, 347–353

[56] References Cited

U.S. PATENT DOCUMENTS

| | | | |
|---|---|---|---|
| 2,577,345 | 12/1951 | McEwen | 128/844 |
| 2,591,783 | 4/1952 | Cruddock | 128/842 |
| 2,670,736 | 3/1954 | Dunkelberger | 128/844 |
| 3,536,066 | 10/1970 | Ludwig | 128/842 |
| 3,648,700 | 3/1972 | Warner | 128/844 |
| 4,664,104 | 5/1987 | Jaicks | 128/844 |
| 4,781,709 | 11/1988 | Grubman | 128/844 |
| 4,834,114 | 5/1989 | Boarman | 128/844 |
| 4,867,176 | 9/1989 | Lash | 128/844 |
| 4,875,490 | 10/1989 | Quiroz | 128/842 |

Primary Examiner—Robert A. Hafer
Assistant Examiner—Michael Brown
Attorney, Agent, or Firm—Morton J. Rosenberg; David I. Klein

[57] ABSTRACT

The contraception and prophylaxis enhancement system (10) is provided for use by women, having a one-piece formation which includes an extended tubular member (12) coupled to a genital shield member (14). Contraceptive system (10) includes an absorbent fluid capturing element (40) disposed within the distal end (30) of tubular member (12). In addition to its fluid absorbing function, absorbent fluid capturing element 40 applies an elastic biasing force to the tubular wall (31) of tubular member (12) for biasing wall (31) against the interior surface of the vaginal cavity, thereby providing a mechanism for retaining tubular member (12) therein. Further, contraceptive system (10) includes a mechanism for inserting tubular member (12) within the vaginal cavity. A tubular container (50) provides both the instrumentality for insertion and placement of tubular member (12) within the vaginal cavity, as well as providing an internal cavity (56) for storage of the prophylactic assembly (11) and the retention straps (18).

18 Claims, 2 Drawing Sheets

CONTRACEPTION AND PROPHYLAXIS ENHANCEMENT SYSTEM

BACKGROUND OF THE INVENTION

1. Field of the Invention

This invention directs itself to contraceptive systems for use by females. In particular, this invention directs itself to contraceptive systems having an extended tubular member for insertion into the vaginal cavity. More in particular, this invention directs itself to contraceptive systems having an extended tubular member secured to a shield-like member. Further, this invention relates to a contraceptive system which incorporates retention straps for releasably coupling the shield-like member to the individual using the contraceptive system. Still further, this invention relates to a contraceptive system which includes an absorbent fluid capturing element disposed within the distal end of the tubular member. Still further, this invention pertains to a contraceptive system having a means for inserting the tubular member within the vaginal cavity. Further, the means for inserting the

2. Prior Art

Contraceptive systems for females having an extended tubular member are well-known in the art. The best prior art known to the Applicant are U.S. Pat. Nos. 87,932; D 288,485; 2,406,600; 2,445,220; 2,525,238; 2,591,783; 2,816,542; 3,536,066; 3,759,254; 4,004,591; 4,036,220; 4,553,968; 4,588,397; 4,664,104; 4,568,340; 3,032,038; 4,232,675; 3,999,550; 1,866,060; 713,900; 2,389,831; 3,677,225; 4,354,494; 4,735,621; and, 4,834,114, and European Patent #0119143, German Patent #0254211, French Patent #0366492, Swiss Patent #117234 and United Kingdom Patent #0264690.

In some prior art references, such as the inventor's previously issued U.S. Pat. No. 4,834,114 there are provided prophylactic systems incorporating shields for use by females. However, this system lacks an absorbent fluid capturing element for preventing seepage of bodily fluids discharged into the tubular member. Such is important to the overall prophylactic concept whereby a barrier is maintained between the genitals of sexual partners and contact with the partner's bodily fluids must be prevented both during and subsequent to use of the device. Further, this prior art system lacks a means for inserting the tubular member within the vaginal cavity. Such means for insertion is important to promote the continued use of such contraceptive systems.

Other prior art systems, such as that disclosed in U.S. Pat. No. 4,393,871 are directed to sponge-like contraceptive devices which are inserted into the vaginal cavity. However, such devices are impregnated with spermicides or other medications, and are not intended to absorb and prevent seepage of discharged bodily fluids.

Other prior art systems direct themselves to various devices having tubular members coupled to retention or support straps, but lack similar means for retaining the tubular member within the vaginal cavity, absorbent fluid capturing elements, and insertion devices for providing an overall system. tubular member within the vaginal cavity also providing means for storage of the contraceptive prior to use.

SUMMARY OF THE INVENTION

A contraception and prophylaxis enhancement system for use by a female is provided. The contraception and prophylaxis enhancement system includes a prophylactic assembly for at least partial insertion into the vaginal cavity and having a dimension sufficient to substantially interface with the vaginal cavity walls. The prophylactic assembly includes an extended first tubular member having a closed distal end and an open proximal end. The contraception and prophylaxis enhancement system further includes a shield structure positionally located contiguous a lower abdominal area of the female user. The shield structure is secured to the prophylactic assembly in an integral one-piece formation. The contraceptive system also includes means for releasably coupling the shield structure to the female's body. Additionally, the contraceptive system includes an absorbent fluid capturing element disposed within the first tubular member for maintaining semen therein.

DESCRIPTION OF THE PREFERRED EMBODIMENTS

Figure 1:
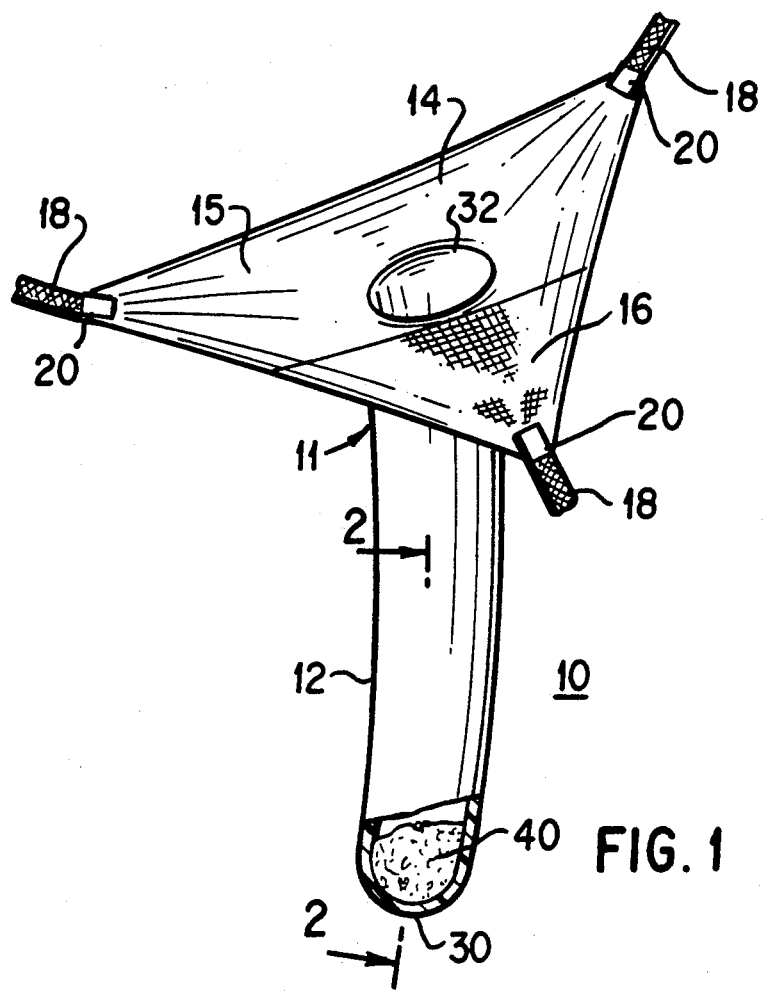
FIG. 1 is a perspective view of the contraceptive system.

Referring to the FIGS., there is shown, system 10 for contraception and prophylaxis enhancement. Contraceptive system 10 is intended to be used by women as a means to aid in the prevention of communicable disease transmission through intimate sexual contact.

In overall concept, contraceptive system 10 provides a condom-like tubular element 12 coupled to a genital shield 14 which enhances the prophylactic properties of the condom-like element 12 as described in U.S. Pat. No. 4,834,114 incorporated herein by reference. Contraceptive system 10 provides a contraceptive method to women which has been proven safe and effective, but has up to now not been successfully adapted for use by women. While the condom is considered the best means for preventing the transmission of venereal-type diseases and simultaneously preventing conception, it has heretofore only been successfully used by men.

Contraceptive system 10 however, enhances and improves on the prior art condom by being adapted for use by women, providing a genital shield to further preclude a chance of disease transmittal through intimate sexual contact and includes an absorbent fluid capturing element for preventing subsequent inadvertent contact with semen.

Genital shield 14 further includes at least one absorbent material layer 16 to further enhance the disease preventive qualities of contraceptive system 10. Additionally, contraceptive system 10 is also provided with an absorbent fluid capturing element 40 disposed within the condom-like element 12 for maintaining semen within the tubular condom-like element 12 to prevent any inadvertent contact therewith during subsequent handling and disposal of system 10. To further enhance the applicability of a condom-like device for use by women, contraceptive system 10 includes a tubular applicator device 50 for providing a means of inserting the condom-like tubular element 12 within the vaginal cavity. This tubular applicator device 50 includes a tubular cavity 56 in which the tubular element 12 and genital shield 14 is stored prior to use.

Referring now to FIG. 1, there is shown contraceptive system 10 for use by women as a means of contraception and prophylaxis. Contraceptive system 10 includes an extended tubular member 12 having a closed distal end 30 for insertion into the vaginal cavity of the female using contraceptive system 10. Tubular member 12 has an open proximal end 32 to permit insertion of the penis of a male sexual partner while maintaining a barrier between the penis and the vaginal cavity walls. The diameter of extended tubular member 12 is approximately 25% larger than the diameter of a conventional condom for use by males. This larger diameter insures contiguous contact between tubular member 12 and the vaginal cavity walls.

As an improvement over prior art condom devices, contraceptive system 10 includes genital shield 14 coupled to the proximal end 32 of tubular member 12. Genital shield 14 is a cuneiform, or wedge-shaped member formed at the proximal end of tubular member 12. Tubular member 12 and genital shield 14 are form of a latex rubber material molded in a one-piece formation by methods well-known in the art.

To further enhance the prophylactic characteristics of contraceptive system 10, an absorbent material 16 is bonded to at least one surface 15 of genital shield 14. Absorbent material 16 is shown in the FIG. as being bonded to a portion of the outside surface of genital shield 14, however, it would be obvious to extend the absorbent material 16 to cover all of the exterior surface 15 of shield 14, or provide separate absorbent material members on both the inside and outside surfaces thereof. When absorbent material 16 is to be placed on both the inside and exterior surface of shield 14 it is important that a fluid resistant barrier be maintained between the absorbent material layers such that fluid absorbed by one layer is not transferred to the other. The composition of absorbent material 16, although not important to the inventive concept, may be any one of a number of cloth or paper compositions having high absorbency.

Contraceptive system 10 includes absorbent fluid capturing element 40 disposed at the distal end 30 of tubular member 12. Absorbent fluid capturing element 40 is a sponge-like element intended to absorb any fluid discharged into tubular member 12 and thus prevent seepage therefrom. This feature is an important enhancement to condom-like systems for use by females, as it substantially prevents contact with bodily fluids which may provide a source of disease transmittal. The sponge-like absorbent element 40 may be provided to the user already disposed within tubular element 12, or in the alternative, as a separately supplied element to be inserted subsequent to or simultaneously with insertion of the tubular member 12 within the vaginal cavity.

Figure 4:
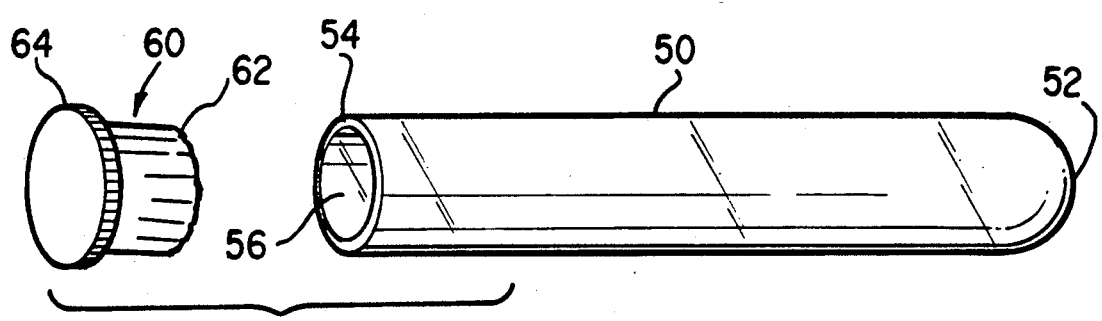

Of particular importance to the inventive concept of contraceptive system 10 is the means for inserting tubular member 12 within the vaginal cavity. Referring to FIG. 4, there is shown a perspective exploded view of the tubular container 50 which provides means for insertion and placement of tubular member 12 within the vaginal cavity, as well as storage thereof. The tubular container 50 has an open proximal end 54 and a closed distal end 52 defining an internal tubular cavity 56 for storage of the remainder of contraceptive system 10 prior to use.

Tubular container 50 has a length dimension which is greater than the length of tubular member 12. The diameter of tubular container 50 must be less than the diameter of tubular member 12, however the diameter must be sufficiently large to provide an adequate volume for storage of the integrally formed shield 14 and tubular member 12, absorbent fluid capturing element 40, as well as any retention straps 18.

A closure 60 is provided for use with tubular container 50. Closure 60 includes an insertable portion 62 which matingly interfaces with the interior wall surface of proximal open end 54 of tubular container 50. The opposing end of closure 60 is provided with a cap portion 64 having a diameter greater than the diameter of tubular container 50. Cap portion 64 provides a stop for limiting the insertion depth of closure 60 and provides a means to grip the closure 60 for withdrawal thereof from tubular container 50. Closure 60 is maintained within the open proximal end 54 of tubular container 50 by techniques well-known in the art, such as being frictionally held therein, or being provided with recesses or projections for a snap-type coupling with cooperating elements formed within the proximal ends 54 of tubular container 50. Obviously, for purposes of commercial packaging, additional sealing elements can be used in combination with closure 60.

In use, the female user of contraceptive system 10 removes the prophylactic assembly 11 from within the tubular cavity 56 of container 50, and places it contiguous the vulval region of her body with tubular member 12 being positioned adjacent the vagina. The closed distal end 52 of tubular container 50 is then inserted into tubular member 12 to provide an applicator for insertion of tubular member 12 into the vaginal cavity. Thus, as the tubular container is inserted into tubular member 12 the tubular member 12 and the container 50 therein are longitudinally displaced a predetermined distance, as determined by the length of tubular member 12, within the vaginal cavity. Subsequent to placement of tubular member 12 within the vaginal cavity, tubular container 50 may be discarded, or further utilized, as will be described in following paragraphs. Tubular container 50 having a diameter less than the diameter of tubular member 12, allows for easy withdrawal of tubular container 50 without causing the withdrawal of tubular member 12. Closure 60 may be coupled to container 50 during this process to facilitate handling of container 50.

Tubular container 50 is formed from a plastic material composition wherein the closed distal end 52 is provided with a semi-spherical contour, so as to be devoid of any sharp corners or edges which might otherwise damage tubular member 12 during the insertion process.

Figure 2:
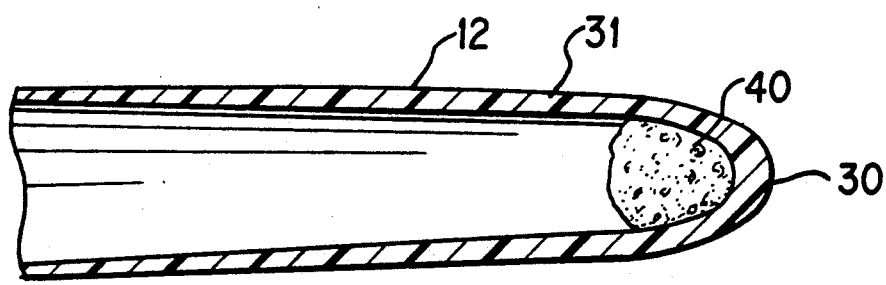
FIG. 2 is a partial cross-sectional view of one embodiment of the contraceptive system taken along the section line 2—2 of FIG. 1.

Referring now to FIG. 2, there is shown a cutaway sectional view of tubular member 12 which clearly shows the non-uniform wall thickness for one embodiment of tubular member 12. The non-uniform thickness of wall 31 of tubular member 12 linearly increases in thickness from proximal end 32 to the closed distal end 30. The thicker wall formed at the distal end 30 provides a means for retaining the tubular member 12 within the vaginal cavity. The increased wall thickness being located at the distal end stiffens the distal end to prevent collapse thereof. Further, the absorbent fluid capturing element 40 has an elastic characteristic which aids in biasing the wall 31 against the interior surface of the vaginal cavity at the distal end 30.

Figure 3:
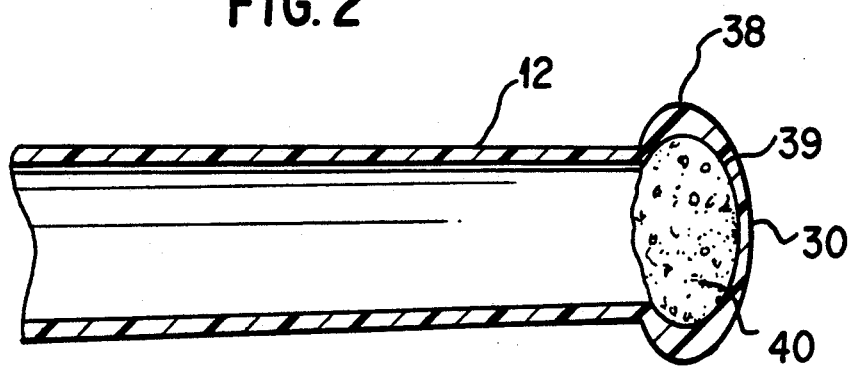
FIG. 3 is a partial sectional view of another embodiment of the contraceptive system taken along the section line 2—2 of FIG. 1; and, FIG. 4 is an exploded perspective view of the insertion and storage assembly of the contraceptive system.

Referring to FIG. 3, there is shown a cutaway sectional view of an alternate embodiment for tubular member 12 wherein the distal end 30 of tubular member 12 is expanded for retaining the tubular member 12 within the vaginal cavity and retaining the absorbent fluid capturing element 40 within the distal end portion of tubular member 12. The closed distal end 30 of tubular member 12 is provided with an enlarged distal portion 38 having a diameter larger than the opposing proximal end 32 of tubular member 12. The enlarged distal portion 38 has a mushroom-shaped contour having a correspondingly shaped cavity 39 for maintaining the absorbent sponge-like fluid capturing element 40 therein.

For the embodiment of FIG. 3, the tubular member 12 is inserted into the vaginal cavity by the method previously described. However, subsequent to insertion thereof, the absorbent fluid capturing element 40 is inserted into the open proximal end 32 of tubular member 12. The tubular container 50 is then reinserted within tubular member 12 to displace the absorbent element 40 toward the distal end 30. Once the absorbent element 40 has been positioned within the cavity 39 the tubular container 50 may be withdrawn and disposed of. The elastic properties of the absorbent element 40 provides expansive forces to the enlarged distal portion 38 of tubular member 12, providing a means for maintaining the tubular member 12 within the vaginal cavity. Obviously, while the expansive forces are sufficient to maintain tubular member 12 within the vaginal cavity under normal conditions, such does not prevent removal of the prophylactic assembly 11. The forces maintaining tubular member 12 within the vaginal cavity can easily be overcome by applying withdrawal forces to the genital shield 14 subsequent to the retention straps 18 being uncoupled therefrom.

The operable location of contraceptive system 10 is further maintained with the aid of retention straps 18 coupled to the vertices of genital shield 14. Retention straps 18 are fastened around the body of the user to assist in maintaining the location of genital shield 14 in proper contact with the vulvar region of the user. Thus, three retention straps 18 are provided, coupled at one end to the shield member 14 and tied or clasped together at the opposing ends. Hence, two straps pass around the waist of the user, while the third passes between the legs to be joined with the two fastened around the waist.

Retention straps 18 may be permanently bonded to shield member 14 with adhesives, ultrasonic bonding or similar techniques. Alternately, each retention strap 18 may be releasably secured to shield member 14 by a clasp 20. Clasp 20 may be a small spring-loaded clamping device, well-known in the apparel art.

In summary, contraception system 10 provides an enhanced system for prophylaxis for use by women. The system comprises a prophylactic assembly 11 having a longitudinally extended tubular member 12 integrally formed in one-piece formation to a genital shield 14. Contraceptive system 10 further includes an absorbent fluid capturing sponge-like element 40 positionally located at the distal end 30 of tubular member 12 for substantially preventing any subsequent leakage of semen from tubular member 12. Additionally, absorbent sponge-like fluid capturing element 40 aids in the retention of tubular member 12 within the vaginal cavity.

Absorbent element 40 has elastic properties that in combination with its size and density aid in biasing the tubular wall of the distal end 30 of tubular member 12 against the inner surface of the vaginal cavity. Further, means may be provided for retaining the absorbent element 40 within tubular member 12. To this end an enlarged distal portion 38 is provided with a cavity 39 into which the absorbent element is disposed. The difference in diameter between the enlarged distal portion and its respective cavity 39 with respect to the remainder of tubular member 12 captures the absorbent element 40 therein. The enlarged distal portion 38 further serves to retain the tubular member 12 within the vaginal cavity.

The tubular container 50 serves the dual function of providing a storage container for the prophylactic assembly 11 and retaining straps 18, as well as providing a means for inserting tubular member 12 within the vaginal cavity and the absorbent fluid capturing element 40 within tubular member 12.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A contraception and prophylaxis enhancement system for use by a female, comprising:
   (a) prophylactic means for at least partial insertion into a vaginal cavity of said female and having a dimension sufficient to substantially interface with a wall of said vaginal cavity, said prophylactic means including an extended first tubular member having a closed digital end and an open proximal end;
   (b) shield means positionally located contiguous a lower abdominal area of said female and being secured to said prophylactic means;
   (c) means for releasably coupling said shield means to said female;
   (d) absorbent fluid capturing means disposed within said extended first tubular member for maintaining semen within said first tubular member; and,
   (e) means for insertion and placement of said first tubular member within said vaginal cavity, said insertion means being defined by a substantially rigid second tubular member having a closed distal end and being reversibly insertable within said first tubular member, said second tubular member having an axially extended cavity formed therein and being accessible through an open proximal end for storage of at least said prophylactic means, said insertion means further including a releasable closure sealingly coupled to said open proximal of said second tubular member.

2. The contraception and prophylaxis enhancement system as recited in claim 1 where said closed distal end of said second tubular member has a substantially semispherically-shaped contour.

3. The contraception and prophylaxis enhancement system as recited in claim 1 where said second tubular member has a predetermined length dimension longer than a length dimension of said first tubular member.

4. The contraception and prophylaxis enhancement system as recited in claim 1 where said first tubular member forms a sheath having a non-uniform wall thickness linearly increasing from said open proximal end to said closed distal end.

5. The contraception and prophylaxis enhancement system as recited in claim 1 where said prophylactic means includes means for retaining said absorbent fluid capturing means within said first tubular member.

6. The contraception and prophylaxis enhancement system as recited in claim 5 where said retaining means is defined by a substantially enlarged closed distal end of said first tubular member for receiving said absorbent fluid capturing means therein.

7. The contraception and prophylaxis enhancement system as recited in claim 6 where said enlarged closed distal end of said first tubular member has a diameter whose dimension is greater than a diameter dimension of said open proximal end of said first tubular member.

8. The contraception and prophylaxis enhancement system as recited in claim 7 where said enlarged closed distal end of said first tubular member has a mushroom-shaped contour.

9. The contraception and prophylaxis enhancement system as recited in claim 8 where said mushroom-shaped closed distal end of said first tubular member defines means for retaining said first tubular member within said vaginal cavity subsequent to insertion of said absorbent fluid capturing means.

10. The contraception and prophylaxis enhancement system as recited in claim 1 where said absorbent fluid capturing means includes a flexible sponge-like member.

11. The contraception and prophylaxis enhancement system as recited in claim 1 where said shield means includes an outer layer of absorbent material formed on at least one side thereof.

12. The contraception and prophylaxis enhancement system as recited in claim 1 where said second tubular member is formed from a plastic material composition.

13. A method for insertion and placement of a condom-like contraception and prophylaxis enhancement system within a human vaginal cavity, said contraception system having a shield for overlaying a vulval region of a female body coupled to a tubular member having a closed distal end, comprising the steps of:
  (a) removing said contraceptive device from a container having a tubular contour and a closed distal end;
  (b) placing said contraception device contiguous said vulval region;
  (c) coupling said shield to said female body; and,
  (d) inserting said closed distal end of said container into said tubular member of said contraception system and substantially simultaneously inserting and displacing said tubular member within said vaginal cavity.

14. The method as recited in claim 13 wherein the step of inserting said closed distal end of said container is preceded by insertion of an absorbent fluid capturing element into said tubular member.

15. The method as recited in claim 13 wherein the step of inserting said closed distal end of said container is followed by the step of withdrawing said container, whereby said tubular member remains positioned within said vaginal cavity.

16. The method as recited in claim 15 wherein the step of withdrawing said container is followed by the step of inserting an absorbent fluid capturing element into said tubular member.

17. The method as recited in claim 16 wherein the step of inserting said absorbent element is followed by the step of reinserting said container for positioning said absorbent element contiguous to said closed distal end of said tubular member.

18. The method as recited in claim 13 wherein the step of coupling said shield includes the step of fastening said shield to at least one retaining strap member encompassing a portion of said female body.

* * * * *